United States Patent [19]

Michelson

[11] Patent Number: 4,968,298
[45] Date of Patent: Nov. 6, 1990

[54] INTERSPACE IRRIGATOR

[76] Inventor: Gary K. Michelson, 438 Sherman Canal, Venice, Calif. 90291

[21] Appl. No.: 242,871

[22] Filed: Sep. 12, 1988

[51] Int. Cl.$^5$ ............................................. A61M 5/178
[52] U.S. Cl. ........................................ 604/36; 604/49; 604/73; 604/75; 604/96; 604/104; 604/187; 604/218; 604/278
[58] Field of Search ................. 604/27, 28, 29, 35–38, 604/41, 49, 54, 97, 99, 104, 109, 187, 190, 218, 239, 278, 96, 73, 75, 101; 128/344, 750

[56] References Cited

U.S. PATENT DOCUMENTS

| | | | |
|---|---|---|---|
| 451,179 | 4/1891 | Ware | 604/75 |
| 3,045,677 | 7/1962 | Wallace | 604/101 |
| 3,046,988 | 7/1962 | Moreau et al. | 604/101 |
| 3,527,203 | 9/1970 | Gravlee | 604/41 |
| 3,633,586 | 1/1972 | Sheridan | 604/96 |
| 3,707,146 | 12/1972 | Cook et al. | 604/96 |
| 4,245,639 | 1/1981 | LaRosa | 604/97 |

*Primary Examiner*—Randall L. Green
*Assistant Examiner*—Randy Shay
*Attorney, Agent, or Firm*—Lewis Anten

[57] ABSTRACT

A suction irrigation device for use in the lumbar interspace following conventional discectomy is disclosed. The device has an inflatable cuff to seal the interspace opening and permit the evacuation of residual disc fragments through a closed system so as to assure that such debris does not find its way into the spinal canal.

14 Claims, 8 Drawing Sheets

FIG. 6
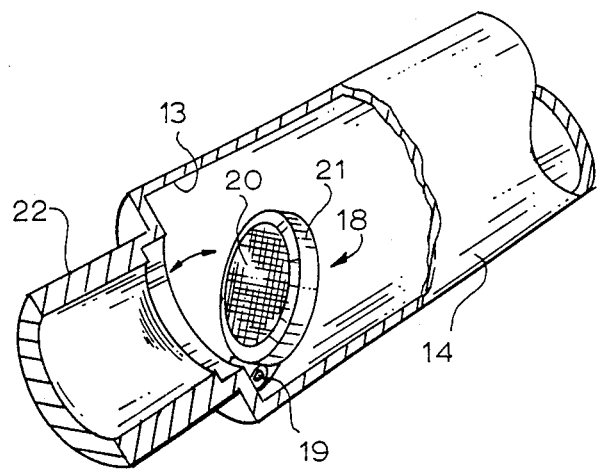
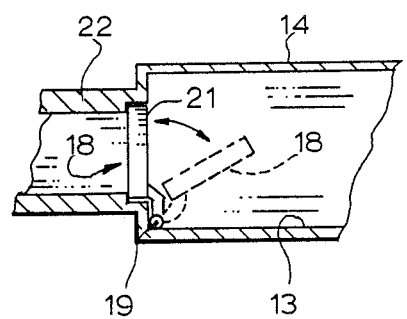
FIG. 6(a)

INTERSPACE IRRIGATOR

BACKGROUND

At the present time lumbar disc herniations with neural compression are almost always operated on from a posterior approach (from behind). Once the disc herniation is surgically exposed the disc itself is generally entered either through a pre-existent hole in the annulus (fibrosis casing of the disc), or an opening is made with a knife. Various instruments are then utilized to either scrape the disc material from between the vertebrae, e.g. currettes; or to bite it, e.g. rongeurs. Because of the presence of the relatively fixed dural sac and the nerve roots which are only minimally mobilizable, the access opening is relatively small in relation to the volume of the disc. During this procedure, the goal is to remove not the entire disc but rather that portion which is at risk to fragment off or reherniate.

Generally, at the completion of the procedure there is a small access window into the disc, lateral to the dural sac and traversing nerve root but medial to the exiting nerve root, and a relatively large disc space, corresponding to the removed portion of the disc, surrounded by the otherwise intact annulus fibrosis and all of the residual nucleus, which is usually rather considerable. Because of the relatively large excavation in relation to the small access opening, it is generally not possible to visualize the entire disc space. Therefore, it is possible for disc fragments to be free in the disc space or to be partially free and only tenuously attached. If not removed, such fragments could, after the surgery, extrude into the spinal canal and either compress or inflame the neural elements, or both, resulting in the failure of the original surgery and resulting in the need for an additional surgery to correct the condition. Such postoperative disc surgeries are quite common and probably occur with a frequency of ten to twenty percent. As is it is not unusual for these patients to at first have experienced relief of all leg pain and then to shortly after being mobilized to have the reherniation, it is generally believed that the residual freed, but not removed, or nearly free fragments are forcefully extruded from the disc space when the disc space is significantly compressed from the patient assuming the seated or standing positions.

At present, therefore, in an attempt to remove such disc fragments during the original surgery and to avoid the above described problems, it is the accepted and customary practice to attempt to irrigate, or wash out, the disc space after the completion of the partial disc removal procedure. Three means are currently used to perform such an irrigation. First, one can take an irrigation bulb (see FIG. 1) and aim it at the disc opening so that as much of the stream of fluid as possible goes into the disc space. Secondly, one can take an ordinary syringe and again aim the stream at the disc opening. Thirdly, one can place the end of a catheter (a small hose) into the disc space itself and then irrigate the space through that small tube.

The first and second above methods are only minimally effective in that the tip of the irrigation source is quite some distance from the opening itself, and even when some portion of the stream passes through the disc opening, the path is determined by the relatively fixed location of the opening and the tip such that the disc space is not effectively irrigated. The third method, while delivering the fluid within the disc space, is also less than optimally effective as it is difficult to direct the tip in a global fashion as would be needed. Also, since it is lacking some means of occluding the entrance to the space, the fluid tends to simply run out of the access opening rather than mobilize the debris fragments.

Unfortunately, to whatever degree the above methods are effective, they are also quite dangerous. Since the opening to the disc space is not occluded during the irrigation process, any fragments successfully mobilized are blown into the spinal canal above, beside, or under the dural sac and nerve roots. If the fragments irrigated from the disc space come to lie beneath the neural elements the surgery may result in a failure. Alternatively, a fragment may follow the path of least resistance and be washed out along the path of the nerve as it exits the spinal canal in the area called the neural foramen. However, there may be insufficient fluid pressure to cause the fragment to exit and the fragment may then plug the passageway compressing the nerve root. Alternatively, as shown in FIG. 2 the fragment may not even make it quite that far and may become trapped by the filmy tissue about the nerve root anywhere within that passageway resulting in a source of irritation to the nerve.

Aware of these undesirable possibilities, it is a common practice following the irrigation of the interspace by one of the known means, as shown in FIG. 3, to then take a 90 degree (right angle) probe and to attempt to blindly feel about beneath the dural sac and nerve roots in the hope of hooking any extruded fragments. While this is sometimes successful, it may instead result in the hidden fragments being actually blindly pushed further beneath the neural structures, thus making these fragments less retrievable and increasing the severity of the neural compression. Furthermore, attempts at blindly sweeping the spinal canal floor are usually met by the disruption of the extremely fragile epidural veins which are a potential source of significant blood loss and later dural compression by the resultant hematomas. Control of the bleeding by electrocoagulation is rarely possible as these vessel ruptures are not accessible, having occurred in the blind area beneath the neural elements or out in the foramen.

In summary then, at present there is clearly a need for a safe and effective means of irrigating the disc space following discectomy.

SUMMARY OF THE PRESENT INVENTION

The present invention consists of a pliable hollow tube with an inflatable cuff at one end. The other end of the tube is connected to a three ring syringe. A small bladder with a one way flap valve is connected via a small hollow tube to the inflatable cuff. The bladder and valve are designed so that when the bladder is squeezed, the valve closes and the inflatable cuff is inflated. A control located in the bladder may be operated so as to open the valve and cause the inflatable cuff to deflate.

Following the discectomy, the pliable hollow tube is placed into the disc space with the cuff in the access opening. The cuff is then inflated so as to close off the access opening. The sealing of the access opening creates an enclosed chamber.

The plunger of the syringe previously loaded with irrigant fluid is then pushed and pulled so that the fragments in the disc space may be effectively mobilized and suctioned into the barrel of the syringe. Once the fragments are pulled into the syringe, they are trapped by a hinged mesh trap, which is pulled up out of the way when the plunger is pulled up and which is pushed downward when the plunger is depressed. Thus, the same fluid can be repumped again and again in and out of the disc space, without risk of returning the fragments into the disc space.

Because the disc space is sealed from the canal, no fluid reflux or iatrogenic extrusion of disc material into the canal can occur, and it is possible to pressurize the disc causing equal fluid pressures in all directions and maximizing the effectiveness of the irrigation process. While the unit is designed to be disposable, it is reusable and can be used repeatedly during the same surgery as in the case of multiple disc herniations.

Finally, the present device allows for the safe sequestration and retention of the fragment specimens which can be easily retrieved from the syringe chamber by removing the plunger.

OBJECTS OF THE PRESENT INVENTION

It is an object of the present invention to provide for a means of irrigating the partially discectomized intervertebral space that is more effective, efficient, and safer.

It is also an object of the present invention to provide for a means of safely and effectively mobilizing nuclear fragments from the disc interspace in a combined irrigation and suction apparatus that is hand operated and requires no extrinsic suction source.

It is another object of the present invention to provide for a means of safeguarding the sanctity of the spinal canal while effectively mobilizing, irrigating, and removing loose nuclear debris.

It is yet another object of the present invention to provide for a means of assuring the one-way transit of nuclear fragments from within the interspace to a retention chamber within the apparatus from which the specimen can easily be removed.

These and other objects and advantages of the present invention will be apparent from a review of the following specification and accompanying drawings.

BRIEF DESCRIPTION OF THE DRAWINGS

FIG. 6 is a partial perspective view of the mesh trap mechanism.

FIG. 6a is a side sectional partial sectional view taken along lines 6a—6a of FIG. 4 of the trap.

DETAILED DESCRIPTION OF THE DRAWINGS

Figure 1:
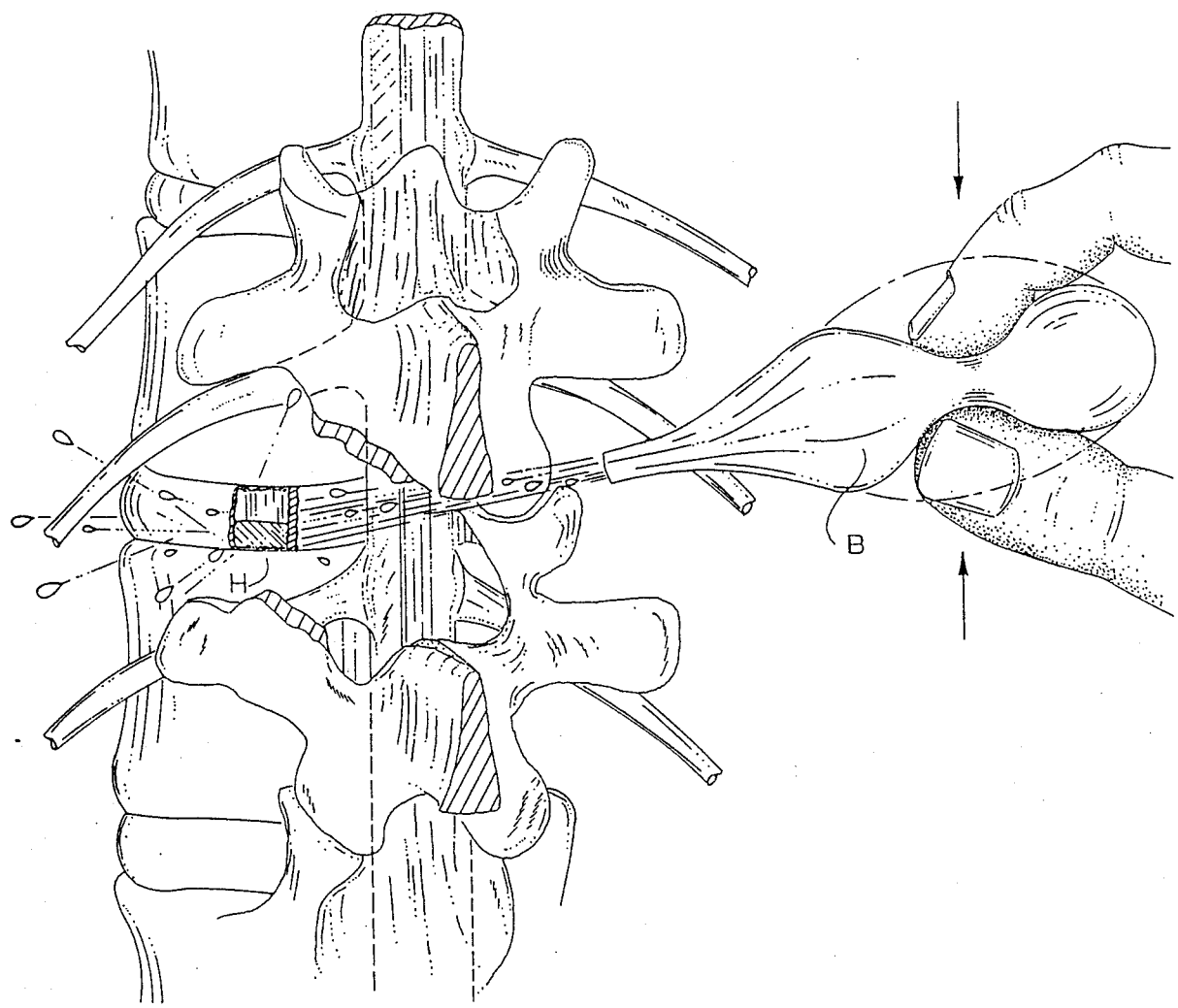
FIG. 1 is a perspective view of prior art irrigation bulb being used to irrigate a lumbar interspace following a partial discectomy.
Figure 2:
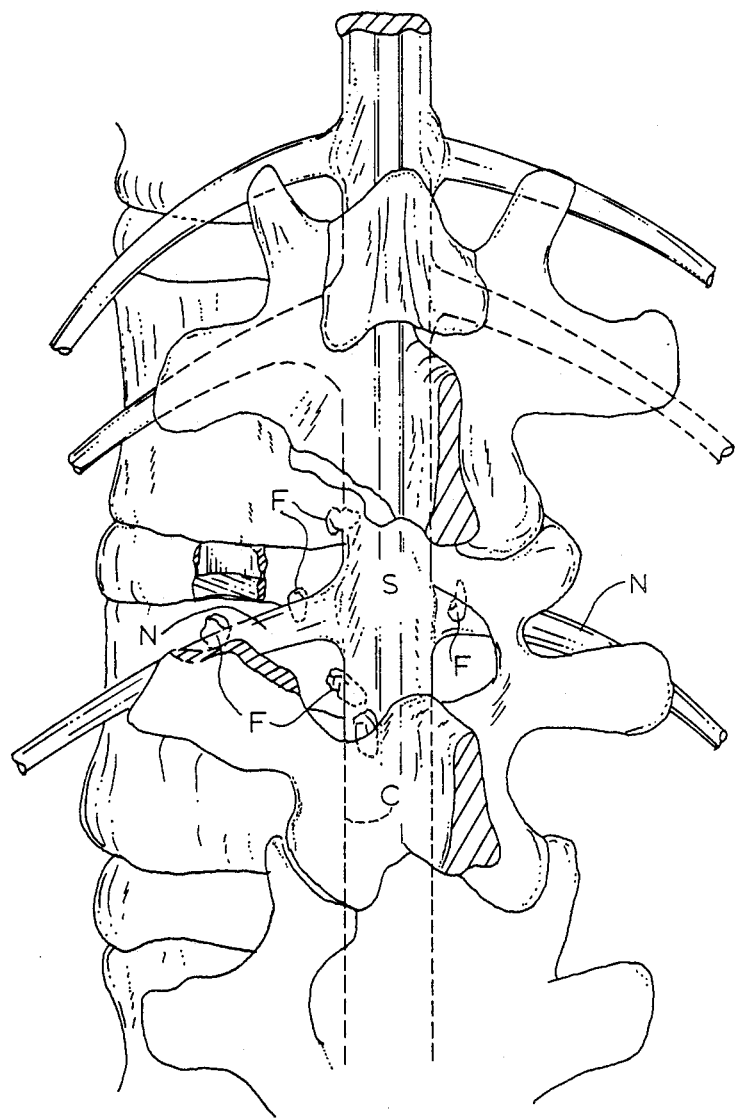
FIG. 2 is a perspective view after irrigation by conventional means, showing nuclear fragments beneath the dura and nerve roots as well as incarcerated in the neuroforamen compressing the nerve root.
Figure 3:
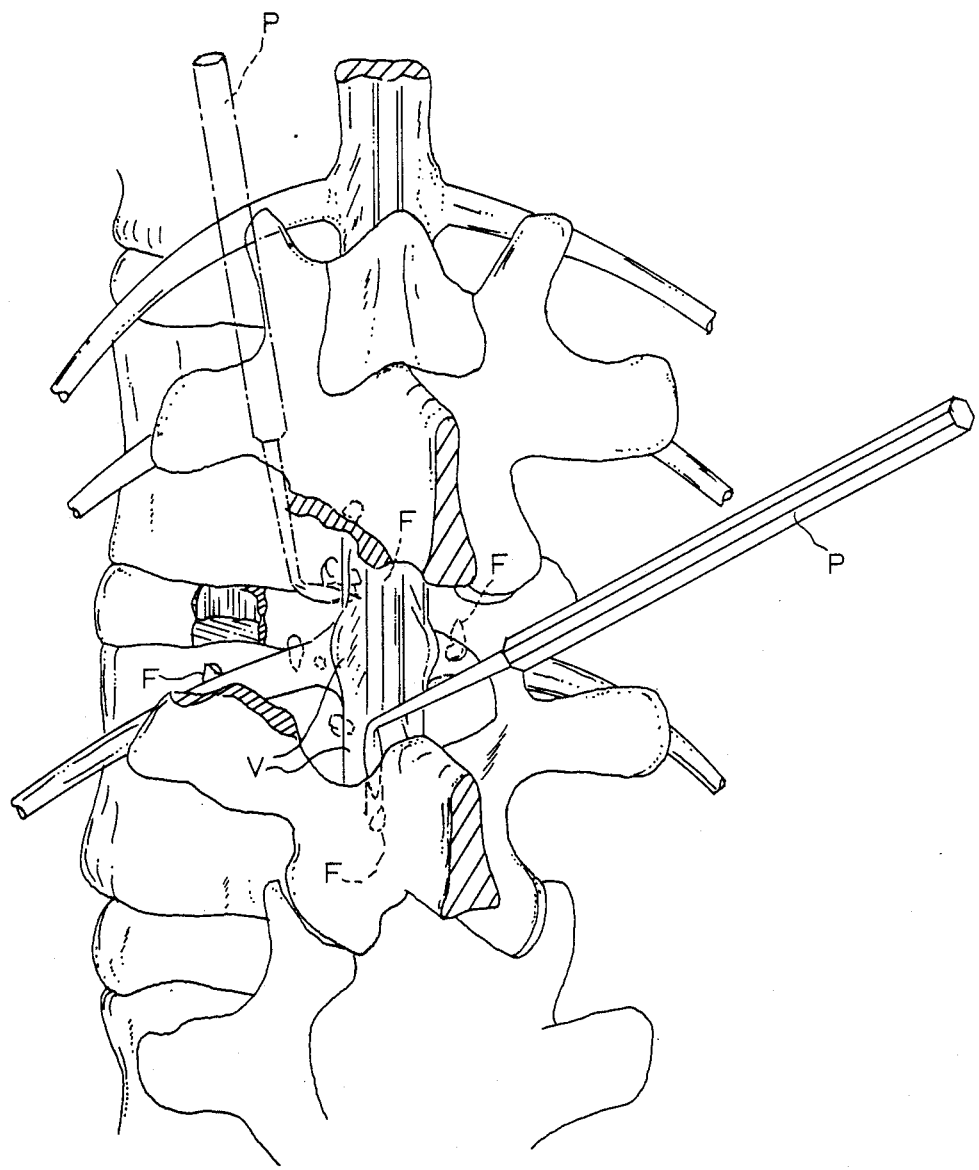
FIG. 3 is a perspective view showing how a dental probe may inadvertently push a disc fragment further under the dura and also rupture the epidural veins.

Referring to FIG. 1 the use of a prior art irrigation bulb B is shown being used to irrigate the disc space D following a partial discectomy. FIG. 2 shows that following such an irrigation by conventional prior art means disc fragments F may become lodged beneath the dural sac S, beneath the nerve N, or become trapped in the nerve root canal C, compressing the nerve root N. FIG. 3 shows how the use of a dental probe P to search, areas not visible through the access opening for loose disc fragments can result in a further sequestration of the disc fragment F and the rupture of epidural veins V.

Figure 4:
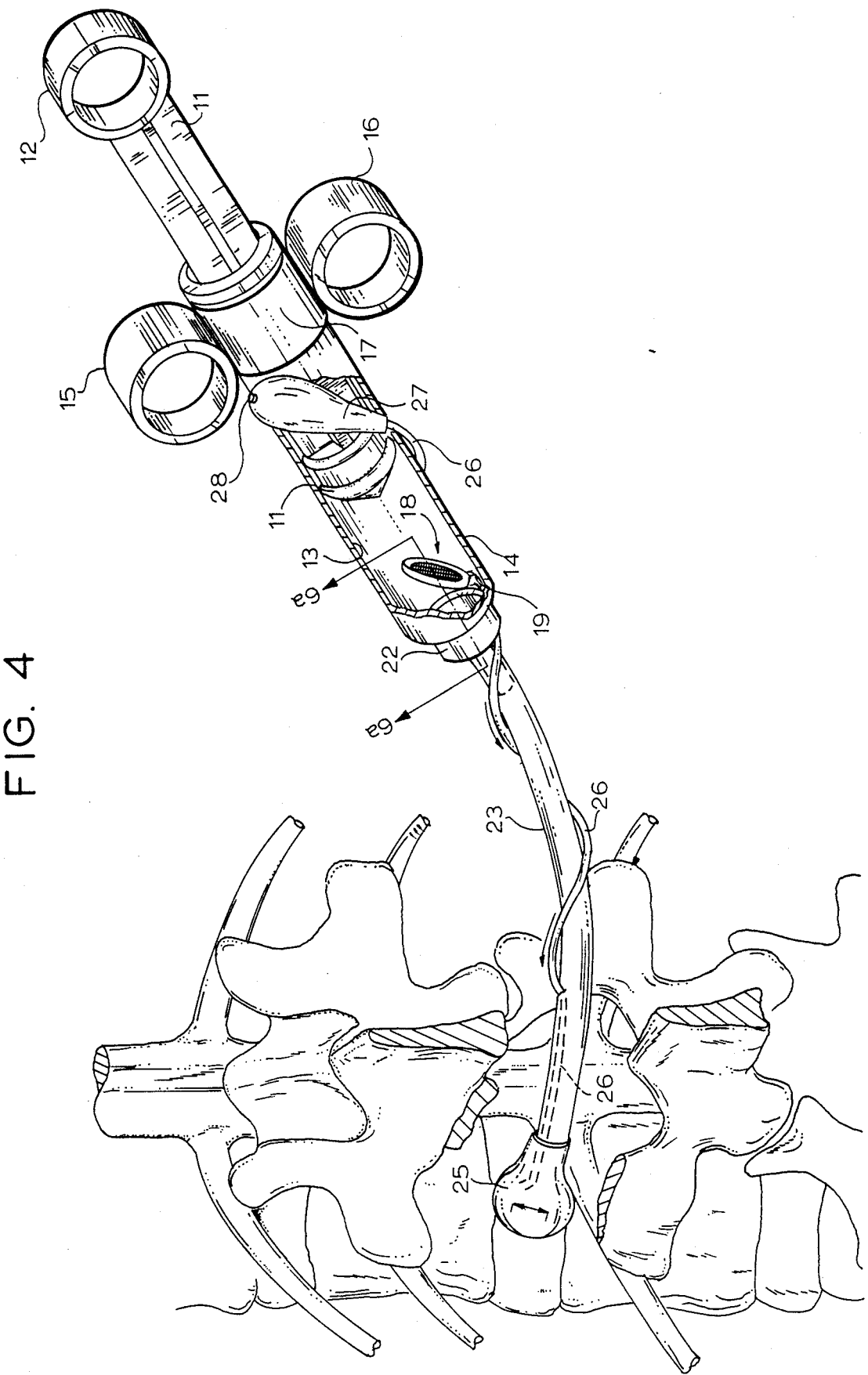
FIG. 4 is a perspective view of the interspace irrigator of the present invention in place and with the cuff inflated.
Figure 4A:
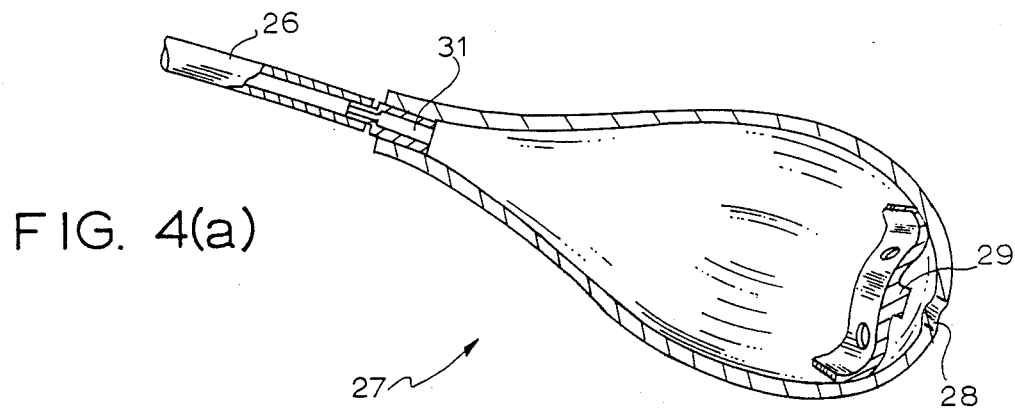
FIG. 4a-4c demonstrates the air bladder mechanism for fitting the cuff.
Figure 4B:
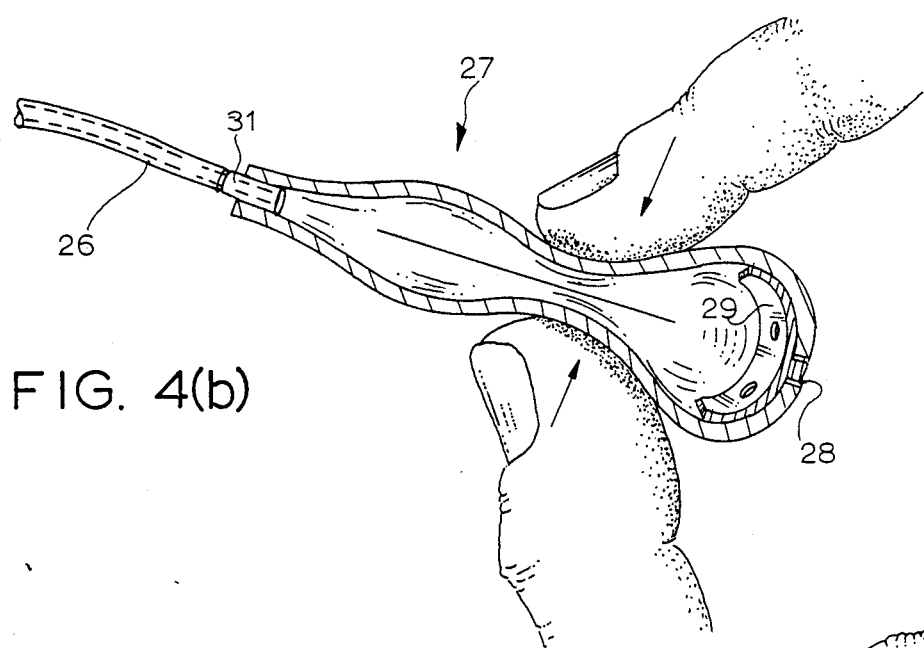
Figure 4C:
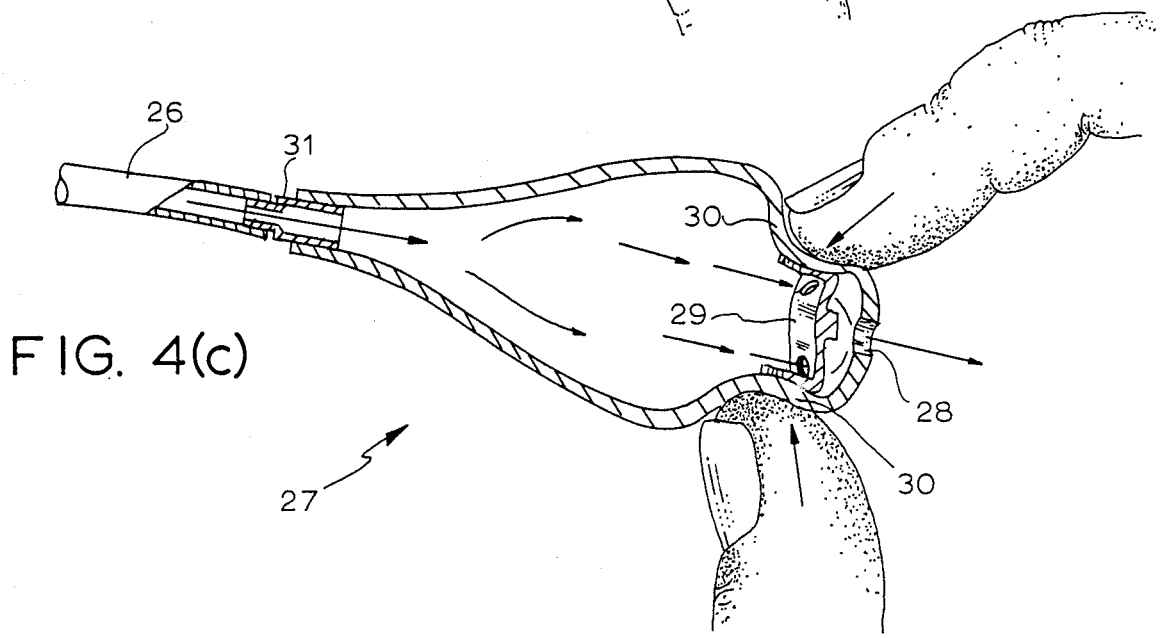

Referring to FIG. 4 the present invention is shown in the interspace. The irrigator consist of syringe S having a plunger 11 with a thumb ring 12. Plunger 11 is able to slide within syringe chamber 13 which is defined by the cylindrical casing 14. Two finger rings 15 and 16 may be integrally molded to casing 14 or attached by means of attachment ring 17.

Contained within the lower end of chamber 13 is a mesh trap ring 18 attached by hinge 19 to the inside casing 14. The trap ring 18 contains a central mesh area 20 and a solid perimeter 21. A long pliant hollow tube 23 made of soft plastic, such as SILASTIC—registered trademark, or an equivalent material is connected to the lower end of chamber 13 by flange 22 the other end of the tube 23 ending with opening 24.

Figure 5:
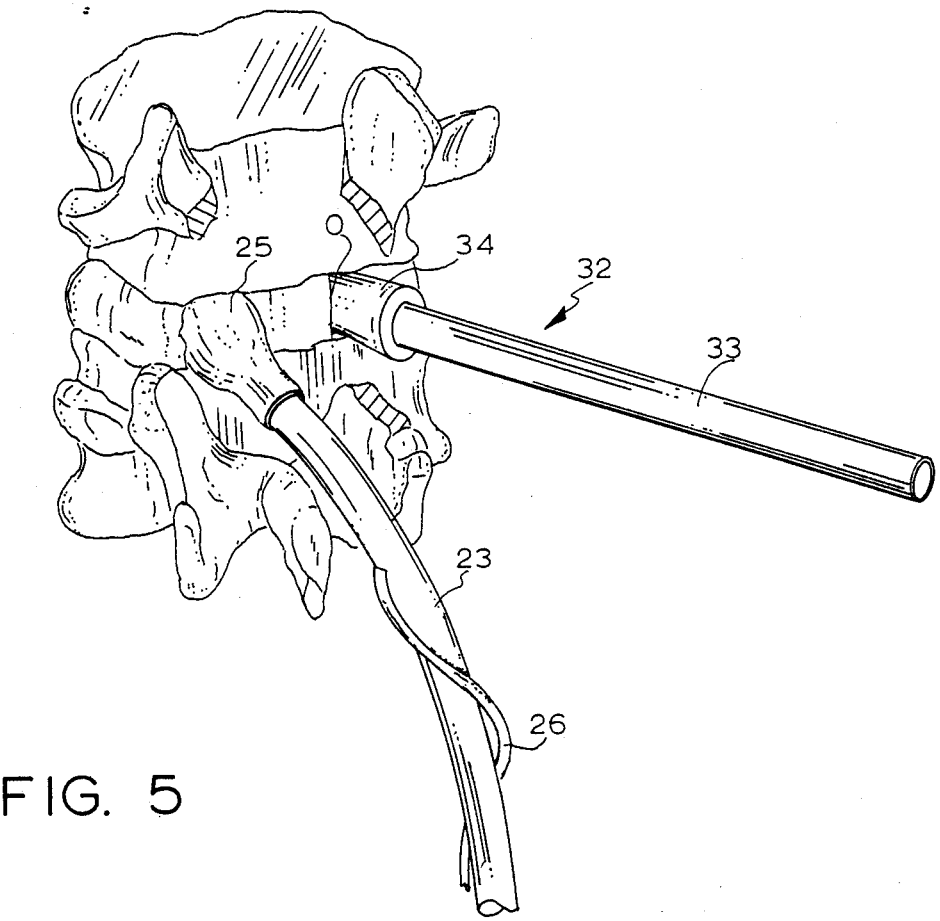
FIG. 5 is a perspective view of the interspace irrigator in place and with the secondary occluder in place on the contralateral side.
Figure 5A:
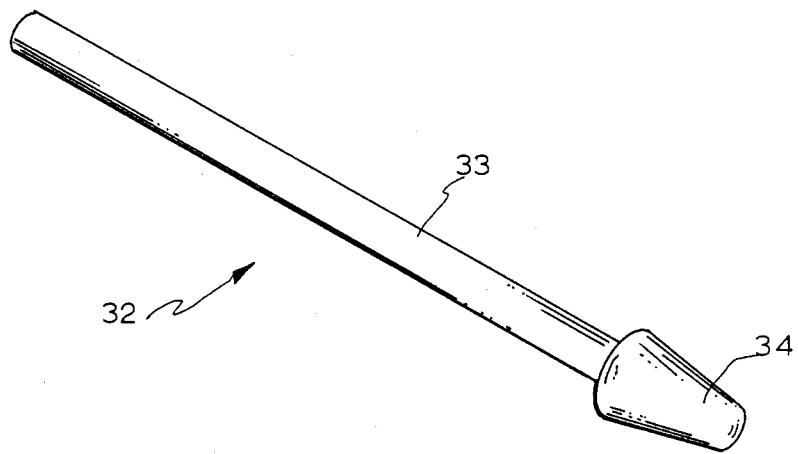
FIG. 5a is a side perspective view of the occluder.

Proximate the opening 24 is an inflatable cuff 25 which surrounds the hollow tube 23. The inflatable cuff, in the preferred embodiment, is merely doughnut shaped, but may also be shaped like a button, mushroom cap, or even be bilobular with a figure eight configuration. This cuff may also be made of foam or gel and be noninflatable. In the preferred embodiment, the interior of the inflatable cuff 25 is connected by small hollow tube 26 to a small air puffing bladder 27 mounted to the syringe. Referring to FIGS. 4–6 bladder 27 is shown as having an opening 28 at one end with a flap valve 29 which sits against the inner bladder end 30. The bladder 27 has an aperture 31 at its other end connecting to tube 26. Tube 26 may be directly connected to the bladder 27.

The operation of the device is as follows: When the irrigator tube end 24 is inserted into the disc pace D the cuff 25 is in its deflated condition. The bladder 27 is then squeezed, causing the air within the bladder to push the flap 29 against the opening 28 thereby forcing all the air within the bladder out opening 31 and down tube 26, thereby inflating cuff 25 and sealing the entrance hole H in the disc space D. Gently squeezing the distal end of the bladder while the bladder is refilling prevents the cuff from spontaneously deflating.

The plunger 11 is then repeatedly pushed and pulled, causing the fluid to enter the disc space, and then be suctioned out of the disc space, along with the disc fragments into the syringe. When fluid is aspirated into the chamber, the mesh ring 18 is pivoted away from the opening in the distal end of the chamber allowing debris to enter the chamber 13. When the fluid is ejected out of the chamber 13 by depressing the plunger 11 then the perimeter of the ring 21 is caught in the pressure change forcing ring 18 to fully seat against the distal end of the chamber 13 allowing the fluid to pass through the central mesh area 20 of ring 18 but the mesh area 20 prevents the escape of any debris from the holding chamber 13. Irrigation of the residual disc fragments through a closed system assures that such fragments do not then find its way into the spinal canal.

After all irrigation has been completed, the cuff 25 is deflated by squeezing the rear of the bladder 27 causing area 30 to push the flap from opening 28 and allowing the bladder to decompress the inflated cuff. Once the inflatable cuff 25 has been deflated irrigation tube 23 may then be withdrawn.

In the preferred embodiment, the length of the chamber 13 of the syringe 5 is approximately 3 inches long, and has a diameter of approximately ⅜ inches. The hollow tube 23 is approximately 6 inches long and has an outside diameter of approximately ¼ inches. The outside diameter of the inflatable cuff, when inflated is large enough to completely fill a ½ inch diameter access opening. However, these dimensions may vary depending on the application of the invention.

The entire bladder and cuff mechanism may be replaced by a cuff of foam, gel, or equivalent resilient material. In the event that the disc has been opened from both the left and right side posteriorly, then the side opposite the irrigator should have the disc space opening 0 occluded with the occluder 32 consisting of a plastic shaft 33 (solid or hollow) and a foam portion 34 which can be placed in the opening 0 to occlude it. The length of shaft 33 is sufficient to allow it to protrude from the wound so that an assistant can maintain its position throughout the irrigation process.

The above described invention may employ a foam portion instead of an inflatable cuff, or any equivalent material that is pliant and can be used to temporarily plug the opening in the disc space. For example, besides air or foam, a gel bladder or bladder filled with water, might be used. Also, when the same disc is opened bilaterally (from both sides) it is necessary to have a means to include the opening opposite the irrigator entrance. For that purpose, the present invention includes a plastic rod with a specially formed foam tip as per FIG. 5 which can be used to temporarily occlude any secondary opening into the interspace to be irrigated.

Figure 6C:
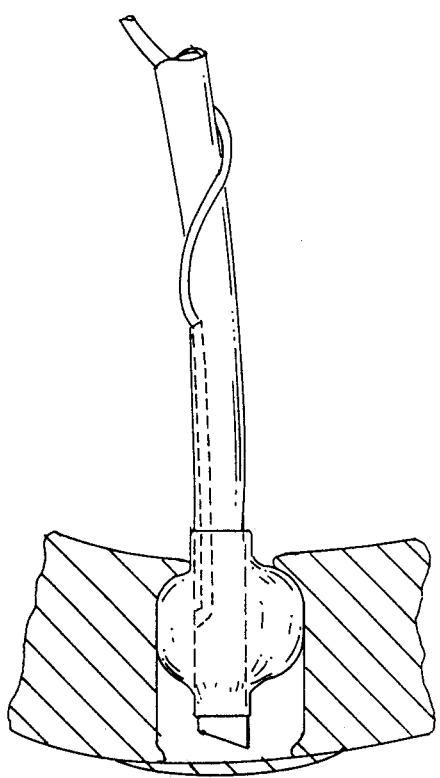
FIGS. 6b through 6e show two alternative embodiments of the inflatable cuff.
Figure 6B:
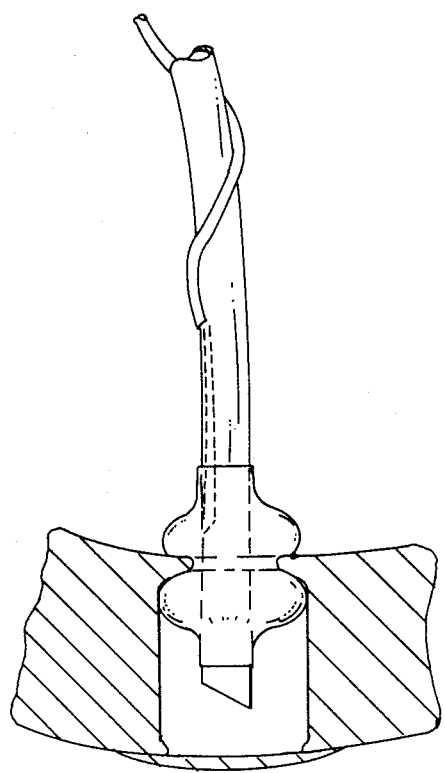
Figure 6E:
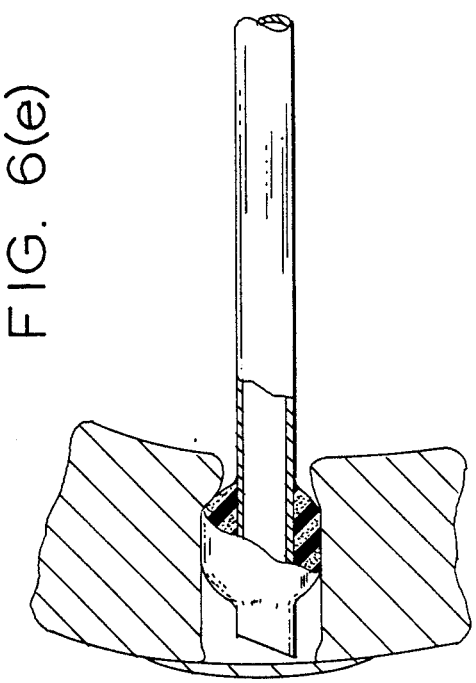
Figure 6D:
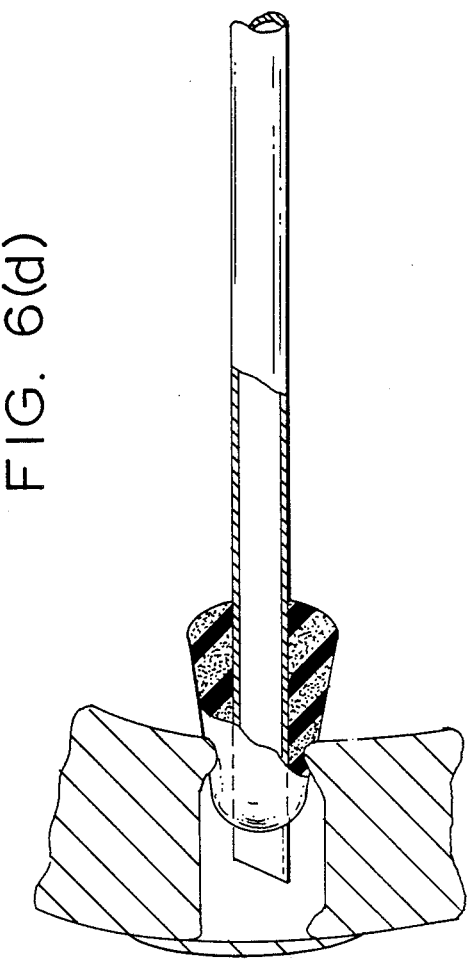

Referring to FIG. 6b, a doughnut shaped cuff is shown. In FIG. 6c a bulb like structure for fitting within the entire disc opening is shown. In FIG. 6d a conical solid cone shaped cuff is shown. And in FIG. 6e, a solid bulb like structure is shown.

It is recognized that other variations of the present invention may be employed which do not depart from the inventive concept of the present invention, but which serves to close the disc opening to create an enclosed chamber which can be washed by the inflow and withdrawal of fluid into the disc space.

What is claimed is:

1. An interspace irrigator for removing disc fragments in a disc space comprising a hollow tubular member, said hollow tubular member having a washing means for injecting irrigation fluid through said hollow tube and for removing irrigation fluid and debris through said hollow tubular member and closure means associated with said hollow tubular member for filling the access opening during a partial discectomy, said washing means comprising an enclosed chamber connected to one end of said hollow tubular member and means for introducing fluid under pressure through said hollow tube and withdrawing fluid through said hollow tubular member and including trap means for trapping fragments of disc material removed by the washing means for preventing them from returning to said disc space.

2. The apparatus of claim 1 in which said washing means comprises a syringe having a plunger connected to one end of said hollow tubular member.

3. The apparatus of claim 1 in which said closure means comprises an inflatable member.

4. The apparatus of claim 3 in which said inflatable member is resilient and may be inflated and deflated after insertion into the access opening.

5. The apparatus of claim 4 in which said inflatable member surrounds said hollow tubular member.

6. The apparatus of claim 3 in which said closure means comprises a resilient member.

7. The apparatus of claim 3 in which said inflatable member has an inflation means, said inflation means comprising a compressible air bladder connected to said inflatable member.

8. The apparatus of claim 7 in which said air bladder has an apperature, said apperature being normally closed and being opened to deflate said inflatable member.

9. The apparatus of claim 7 in which said air bladder includes a two way air valve.

10. The apparatus of claim 1 in which said closure means comprises a solid member.

11. The apparatus of claim 1 in which said closure means has a narrowed diameter portion between two larger diameter portions.

12. A method of washing a disc space having an access created by a partial discectomy comprising the steps inserting a hollow tubular member connected at one end to a syringe filled with a washing fluid, and having a surrounding inflatable member proximate the other end, in the disc space; inflating the inflatable member whereby the inflatable member fills the access opening; inflating the inflatable member; pushing and pulling the plunger of the syringe; deflating the inflatable member; and removing the tubular member.

13. An interspace irragator for removing disc fragments in a disc space comprising a hollow tubular member, said hollow tubular member having washing means for injecting irragation fluid through said hollow tube and for removing irragation fluid said debris through said hollow tubular member and closure means associated with said hollow tubular member for filling the access opening during a partial discectomy, said washing means comprising a syringe having a plunger connected to one end of said hollow tubular member and including a trap means for trapping fragments of disc material removed by the washing means for preventing them from returing to said disc space.

14. The apparatus of claim 13 in which said trap comprises a mesh pivotally mounted on one side within the chamber of said syring, said mesh being movable upwardly during the upward stroke of the plunger and held down during the downward stroke of the plunger.

* * * * *